(12) United States Patent
Jorgensen et al.

(10) Patent No.: US 7,700,338 B2
(45) Date of Patent: Apr. 20, 2010

(54) CGTASE AND DNA SEQUENCE ENCODING SAME

(75) Inventors: Per Lina Jorgensen, Copenhagen (DK); Claus Crone Fuglsang, Vekso (DK)

(73) Assignee: Novozymes A/S, Bagsvaerd (DK)

( * ) Notice: Subject to any disclaimer, the term of this patent is extended or adjusted under 35 U.S.C. 154(b) by 1992 days.

(21) Appl. No.: 10/332,937

(22) PCT Filed: Jul. 13, 2001

(86) PCT No.: PCT/DK01/00494

§ 371 (c)(1),
(2), (4) Date: Jan. 14, 2003

(87) PCT Pub. No.: WO02/06508

PCT Pub. Date: Jan. 24, 2002

(65) Prior Publication Data

US 2003/0170696 A1  Sep. 11, 2003

Related U.S. Application Data

(60) Provisional application No. 60/221,470, filed on Jul. 26, 2000, provisional application No. 60/221,344, filed on Jul. 26, 2000.

(30) Foreign Application Priority Data

Jul. 19, 2000 (DK) ............................... 2000-01116
Jul. 24, 2000 (DK) ............................... 2000-01128

(51) Int. Cl.
*C12N 9/10* (2006.01)
*C12N 15/54* (2006.01)

(52) U.S. Cl. ..................... 435/193; 536/23.2
(58) Field of Classification Search ................ 435/4, 435/6, 69.1, 183, 193, 252.3, 252.31, 320.1; 536/23–24
See application file for complete search history.

(56) References Cited

U.S. PATENT DOCUMENTS 5,409,824 A    4/1995  Schmid
6,004,790 A   12/1999  Dijkhuizen

FOREIGN PATENT DOCUMENTS

DE         4009822       10/1991
WO      WO 91/14770      10/1991
WO      WO 98/13479       4/1998

OTHER PUBLICATIONS

Ohdan et al., Appl. Microbial Biotechnol. vol. 53: pp. 430-434. (2000).
Kim et al., FEMS Microbiology Letters, vol. 164, pp. 411-418. (1998).
Patent Abstract of Japan, Pub. No. 05-244945, Date of Pub: Sep. 24, 1993.

*Primary Examiner*—Rebecca E. Prouty
(74) *Attorney, Agent, or Firm*—Michael W Krenicky

(57) ABSTRACT

The invention relates to isolated CGTases and isolated nucleic acid sequences encoding the CGTases. The invention also relates to nucleic acid constructs, vectors, and host cells comprising the nucleic acid sequences as well as methods for producing and using the CGTases, in particular to cleaning and detergent composition comprising such CGTases.

9 Claims, 3 Drawing Sheets

SEQUENCE LISTING

```
<160> NUMBER OF SEQ ID NOS: 12

<210> SEQ ID NO 1
<211> LENGTH: 2631
<212> TYPE: DNA
<213> ORGANISM: Bacillus agaradhaerans
<220> FEATURE:
<221> NAME/KEY: mat_peptide
<222> LOCATION: (103)..()
<223> OTHER INFORMATION:
<220> FEATURE:
<221> NAME/KEY: CDS
<222> LOCATION: (1)..(2139)
<223> OTHER INFORMATION:

<400> SEQUENCE: 1 atg agg aaa aag act cta aag agg ttg tta act ttg gta gta ggg tta        48
Met Arg Lys Lys Thr Leu Lys Arg Leu Leu Thr Leu Val Val Gly Leu
                -30                 -25                 -20 gtt att ttg agt gga tta agt ata cta gat ttt tct ata aca agt gca        96
Val Ile Leu Ser Gly Leu Ser Ile Leu Asp Phe Ser Ile Thr Ser Ala
            -15                 -10                  -5 agt gca cag caa gca aca gat cgt tca aat agt gta aac tat tca aca       144
Ser Ala Gln Gln Ala Thr Asp Arg Ser Asn Ser Val Asn Tyr Ser Thr
         -1  1                   5                      10 gat gtc att tat caa att gta aca gat agg ttt tac gat ggt gat gaa       192
Asp Val Ile Tyr Gln Ile Val Thr Asp Arg Phe Tyr Asp Gly Asp Glu
 15                  20                  25                  30 agt aac aac cca tca gga gaa ctt tat tcg gaa gat tgt aaa aac tta       240
Ser Asn Asn Pro Ser Gly Glu Leu Tyr Ser Glu Asp Cys Lys Asn Leu
                 35                  40                  45 aga aaa tat tgt ggt gga gat tgg caa ggg ata ata gat aaa ata gat       288
Arg Lys Tyr Cys Gly Gly Asp Trp Gln Gly Ile Ile Asp Lys Ile Asp
             50                  55                  60 gat ggt tat cta acg aac atg ggt gtg acg gca cta tgg atc tca ccc       336
Asp Gly Tyr Leu Thr Asn Met Gly Val Thr Ala Leu Trp Ile Ser Pro
         65                  70                  75 cca gtt gaa aat att ttt gaa acg att gat gat gag ttt ggg aca act       384
Pro Val Glu Asn Ile Phe Glu Thr Ile Asp Asp Glu Phe Gly Thr Thr
```

|     |     |     |     |     |     |     |     |     |     |     |     |     |     |     |      |
| --- | --- | --- | --- | --- | --- | --- | --- | --- | --- | --- | --- | --- | --- | --- | ---- |
|     |     | 80  |     |     |     |     | 85  |     |     |     |     | 90  |     |     |      |
| tct | tat | cac | ggt | tat | tgg | gca | cga | gat | tat | aag | aaa | acg | aac | cct | ttt  | 432 |
| Ser | Tyr | His | Gly | Tyr | Trp | Ala | Arg | Asp | Tyr | Lys | Lys | Thr | Asn | Pro | Phe  |
| 95  |     |     |     | 100 |     |     |     |     | 105 |     |     |     |     | 110 |      |
| ttc | gga | agc | aca | gaa | gat | ttt | gaa | agg | tta | ata | gaa | act | gca | cat | agt  | 480 |
| Phe | Gly | Ser | Thr | Glu | Asp | Phe | Glu | Arg | Leu | Ile | Glu | Thr | Ala | His | Ser  |
|     |     |     |     | 115 |     |     |     |     | 120 |     |     |     |     | 125 |      |
| cac | gat | att | aaa | att | gtt | att | gat | tta | gct | cct | aac | cat | aca | tca | cct  | 528 |
| His | Asp | Ile | Lys | Ile | Val | Ile | Asp | Leu | Ala | Pro | Asn | His | Thr | Ser | Pro  |
|     |     |     | 130 |     |     |     |     | 135 |     |     |     |     | 140 |     |      |
| gca | gat | ttt | gat | aat | cct | gac | tat | gcc | gaa | aat | ggt | gtc | tta | tat | gat  | 576 |
| Ala | Asp | Phe | Asp | Asn | Pro | Asp | Tyr | Ala | Glu | Asn | Gly | Val | Leu | Tyr | Asp  |
|     |     | 145 |     |     |     |     | 150 |     |     |     |     | 155 |     |     |      |
| gat | ggt | aac | tat | ttg | ggt | tcg | tat | tca | gat | gat | tct | gat | tta | ttt | tta  | 624 |
| Asp | Gly | Asn | Tyr | Leu | Gly | Ser | Tyr | Ser | Asp | Asp | Ser | Asp | Leu | Phe | Leu  |
|     | 160 |     |     |     |     | 165 |     |     |     |     | 170 |     |     |     |      |
| tat | aac | ggc | gga | aca | gat | ttc | tct | aac | tac | gaa | gat | gag | att | tat | aga  | 672 |
| Tyr | Asn | Gly | Gly | Thr | Asp | Phe | Ser | Asn | Tyr | Glu | Asp | Glu | Ile | Tyr | Arg  |
| 175 |     |     |     |     | 180 |     |     |     |     | 185 |     |     |     |     | 190  |
| aat | ttg | ttt | gac | tta | gct | agt | ttt | aat | cat | atc | aac | tct | gag | ttg | aat  | 720 |
| Asn | Leu | Phe | Asp | Leu | Ala | Ser | Phe | Asn | His | Ile | Asn | Ser | Glu | Leu | Asn  |
|     |     |     |     | 195 |     |     |     |     | 200 |     |     |     |     | 205 |      |
| aat | tat | tta | gaa | gat | gca | gtg | aaa | aaa | tgg | tta | gat | tta | ggt | ata | gac  | 768 |
| Asn | Tyr | Leu | Glu | Asp | Ala | Val | Lys | Lys | Trp | Leu | Asp | Leu | Gly | Ile | Asp  |
|     |     |     | 210 |     |     |     |     | 215 |     |     |     |     | 220 |     |      |
| ggg | att | cgc | atc | gat | gct | gta | gct | cac | atg | cca | cca | ggt | tgg | aaa | aaa  | 816 |
| Gly | Ile | Arg | Ile | Asp | Ala | Val | Ala | His | Met | Pro | Pro | Gly | Trp | Lys | Lys  |
|     |     | 225 |     |     |     |     | 230 |     |     |     |     | 235 |     |     |      |
| gct | tac | atg | gat | act | ata | tat | gac | cac | aga | gcg | gta | ttt | act | ttt | gga  | 864 |
| Ala | Tyr | Met | Asp | Thr | Ile | Tyr | Asp | His | Arg | Ala | Val | Phe | Thr | Phe | Gly  |
|     | 240 |     |     |     |     | 245 |     |     |     |     | 250 |     |     |     |      |
| gaa | tgg | ttt | act | gga | cct | tct | gga | aat | gag | gat | tac | act | aaa | ttt | gca  | 912 |
| Glu | Trp | Phe | Thr | Gly | Pro | Ser | Gly | Asn | Glu | Asp | Tyr | Thr | Lys | Phe | Ala  |
| 255 |     |     |     |     | 260 |     |     |     |     | 265 |     |     |     |     | 270  |
| aat | aat | agt | ggc | atg | agt | gta | tta | gat | ttc | cgc | ttt | gct | caa | act | aca  | 960 |
| Asn | Asn | Ser | Gly | Met | Ser | Val | Leu | Asp | Phe | Arg | Phe | Ala | Gln | Thr | Thr  |
|     |     |     |     | 275 |     |     |     |     | 280 |     |     |     |     | 285 |      |
| cga | aat | gtc | atc | ggt | aac | aat | aat | gga | acg | atg | tat | gat | att | gaa | aag  | 1008 |
| Arg | Asn | Val | Ile | Gly | Asn | Asn | Asn | Gly | Thr | Met | Tyr | Asp | Ile | Glu | Lys  |
|     |     |     | 290 |     |     |     |     | 295 |     |     |     |     | 300 |     |      |
| atg | cta | aca | gac | aca | gag | aat | gac | tat | gat | cgt | cct | caa | gat | caa | gtt  | 1056 |
| Met | Leu | Thr | Asp | Thr | Glu | Asn | Asp | Tyr | Asp | Arg | Pro | Gln | Asp | Gln | Val  |
|     |     | 305 |     |     |     |     | 310 |     |     |     |     | 315 |     |     |      |
| act | ttt | ctt | gat | aat | cat | gac | atg | agt | cga | ttt | acg | aat | ggt | ggt | gaa  | 1104 |
| Thr | Phe | Leu | Asp | Asn | His | Asp | Met | Ser | Arg | Phe | Thr | Asn | Gly | Gly | Glu  |
|     | 320 |     |     |     |     | 325 |     |     |     |     | 330 |     |     |     |      |
| tca | aca | cgg | aca | aca | gat | att | gga | tta | gcc | tta | atg | ctt | aca | tct | cgt  | 1152 |
| Ser | Thr | Arg | Thr | Thr | Asp | Ile | Gly | Leu | Ala | Leu | Met | Leu | Thr | Ser | Arg  |
| 335 |     |     |     |     | 340 |     |     |     |     | 345 |     |     |     |     | 350  |
| ggg | gtg | cct | act | att | tat | tat | gga | aca | gaa | caa | tac | atg | aaa | ggt | gat  | 1200 |
| Gly | Val | Pro | Thr | Ile | Tyr | Tyr | Gly | Thr | Glu | Gln | Tyr | Met | Lys | Gly | Asp  |
|     |     |     |     | 355 |     |     |     |     | 360 |     |     |     |     | 365 |      |
| gga | gat | cca | gga | agc | agg | gga | atg | atg | gca | tct | ttt | gat | gaa | aat | aca  | 1248 |
| Gly | Asp | Pro | Gly | Ser | Arg | Gly | Met | Met | Ala | Ser | Phe | Asp | Glu | Asn | Thr  |
|     |     |     | 370 |     |     |     |     | 375 |     |     |     |     | 380 |     |      |
| gat | gct | tat | aag | cta | att | caa | aaa | tta | gca | ccg | tta | aga | aaa | agt | aat  | 1296 |
| Asp | Ala | Tyr | Lys | Leu | Ile | Gln | Lys | Leu | Ala | Pro | Leu | Arg | Lys | Ser | Asn  |
|     |     | 385 |     |     |     |     | 390 |     |     |     |     | 395 |     |     |      |
| cct | gca | tat | gga | tat | gga | aca | acg | aca | gaa | cgt | tgg | ata | aac | gat | gat  | 1344 |

```
Pro Ala Tyr Gly Tyr Gly Thr Thr Glu Arg Trp Ile Asn Asp Asp
    400             405                 410 gtc ctc att tat gaa aga cat ttt ggc gag aac tat gct tta atc gcc    1392
Val Leu Ile Tyr Glu Arg His Phe Gly Glu Asn Tyr Ala Leu Ile Ala
415             420                 425                 430 ata aat aga agc tta aat acc tcc tat aat atc caa ggg tta caa aca    1440
Ile Asn Arg Ser Leu Asn Thr Ser Tyr Asn Ile Gln Gly Leu Gln Thr
                435                 440                 445 gag atg cca tcc aat tca tat gat gat gta tta gat gga tta ttg gat    1488
Glu Met Pro Ser Asn Ser Tyr Asp Asp Val Leu Asp Gly Leu Leu Asp
            450                 455                 460 ggg caa tca att gtt gtt gat aac aaa ggg gga gtt aat gaa ttt caa    1536
Gly Gln Ser Ile Val Val Asp Asn Lys Gly Gly Val Asn Glu Phe Gln
        465                 470                 475 atg tct cct gga gag gtg agt gta tgg gaa ttt gaa gcg gaa aat gta    1584
Met Ser Pro Gly Glu Val Ser Val Trp Glu Phe Glu Ala Glu Asn Val
    480                 485                 490 gac aag cct tca att gga caa gtt ggc cca ata att ggt gag gca gga    1632
Asp Lys Pro Ser Ile Gly Gln Val Gly Pro Ile Ile Gly Glu Ala Gly
495             500                 505                 510 cga act gtt aca ata agt gga gaa ggt ttc ggt tct tcg cag ggg act    1680
Arg Thr Val Thr Ile Ser Gly Glu Gly Phe Gly Ser Ser Gln Gly Thr
                515                 520                 525 gtt cac ttt gga tcc act tca gca gaa atc ctt tct tgg aat gat acg    1728
Val His Phe Gly Ser Thr Ser Ala Glu Ile Leu Ser Trp Asn Asp Thr
            530                 535                 540 atc att acc tta act gtg ccg aac aat gaa gcg gga tac cat gat atc    1776
Ile Ile Thr Leu Thr Val Pro Asn Asn Glu Ala Gly Tyr His Asp Ile
        545                 550                 555 act gtt gta aca gaa gat gaa caa gta agt aat gcc tat gaa ttc gaa    1824
Thr Val Val Thr Glu Asp Glu Gln Val Ser Asn Ala Tyr Glu Phe Glu
    560                 565                 570 gtt ctt acg gcc gat caa gtc aca gtt cgt ttt atc ata gac aat gca    1872
Val Leu Thr Ala Asp Gln Val Thr Val Arg Phe Ile Ile Asp Asn Ala
575             580                 585                 590 gaa acg aag ctg ggt gaa aac gtt ttc ctt gta ggt aac gtt cat gaa    1920
Glu Thr Lys Leu Gly Glu Asn Val Phe Leu Val Gly Asn Val His Glu
                595                 600                 605 tta gga aat tgg gat cca gaa caa tca gtt ggg aga ttt ttc aat caa    1968
Leu Gly Asn Trp Asp Pro Glu Gln Ser Val Gly Arg Phe Phe Asn Gln
            610                 615                 620 att gta tac caa tat cca aca tgg tat tat gat gtg aat gtt cct gca    2016
Ile Val Tyr Gln Tyr Pro Thr Trp Tyr Tyr Asp Val Asn Val Pro Ala
        625                 630                 635 aat aca gac tta gaa ttc aag ttt att aaa ata gat caa gat aat aac    2064
Asn Thr Asp Leu Glu Phe Lys Phe Ile Lys Ile Asp Gln Asp Asn Asn
    640                 645                 650 gtc att tgg cag agt gga gct aat caa acc tat tct tca cca gaa agt    2112
Val Ile Trp Gln Ser Gly Ala Asn Gln Thr Tyr Ser Ser Pro Glu Ser
655             660                 665                 670 gga act ggt att ata aga gtt gat tgg tgagtacact cgaagacaaa          2159
Gly Thr Gly Ile Ile Arg Val Asp Trp
                675 taaattctta aaacgaatgt atacacttaa ttaaaaaaag cggcttaaat gcgagcaatt  2219 aaactagaag agtgatacct accaacttat tggttaaggt accactcttc attttttcatt 2279 taagtgagct aaaaggatta ctactaatcc agactataat catcgaaaaa agattccgtc  2339 cattaaagta ggatgagcgg ggtctttttt ggtgaaatcc cgcttttat atgccaactt   2399
```

```
ctcaataggg ggaatcccga tctgtgaagt cagtcgtaat agtttgctag aagagttgct    2459
gaaaaatcag gtggagttgc tgaaaattaa ggggagttac tgaaaaaatc agagttaatg    2519
ctgaagatta agtgtttgtt gctgataaat tgaatagaga tgctgaaaat gcccttttcaa   2579 taacttattt aataattttg gtaataaatt tgccatattt accccttttcg ag            2631
```

<210> SEQ ID NO 2
<211> LENGTH: 713
<212> TYPE: PRT
<213> ORGANISM: Bacillus agaradhaerans

<400> SEQUENCE: 2

```
Met Arg Lys Lys Thr Leu Lys Arg Leu Leu Thr Leu Val Val Gly Leu
            -30                 -25                 -20

Val Ile Leu Ser Gly Leu Ser Ile Leu Asp Phe Ser Ile Thr Ser Ala
        -15                 -10                  -5

Ser Ala Gln Gln Ala Thr Asp Arg Ser Asn Ser Val Asn Tyr Ser Thr
     -1  1               5                  10

Asp Val Ile Tyr Gln Ile Val Thr Asp Arg Phe Tyr Asp Gly Asp Glu
 15                  20                  25                  30

Ser Asn Asn Pro Ser Gly Glu Leu Tyr Ser Glu Asp Cys Lys Asn Leu
                 35                  40                  45

Arg Lys Tyr Cys Gly Gly Asp Trp Gln Gly Ile Ile Asp Lys Ile Asp
             50                  55                  60

Asp Gly Tyr Leu Thr Asn Met Gly Val Thr Ala Leu Trp Ile Ser Pro
             65                  70                  75

Pro Val Glu Asn Ile Phe Glu Thr Ile Asp Asp Glu Phe Gly Thr Thr
 80                  85                  90

Ser Tyr His Gly Tyr Trp Ala Arg Asp Tyr Lys Lys Thr Asn Pro Phe
 95                 100                 105                 110

Phe Gly Ser Thr Glu Asp Phe Glu Arg Leu Ile Glu Thr Ala His Ser
                115                 120                 125

His Asp Ile Lys Ile Val Ile Asp Leu Ala Pro Asn His Thr Ser Pro
            130                 135                 140

Ala Asp Phe Asp Asn Pro Asp Tyr Ala Glu Asn Gly Val Leu Tyr Asp
            145                 150                 155

Asp Gly Asn Tyr Leu Gly Ser Tyr Ser Asp Asp Ser Asp Leu Phe Leu
160                 165                 170

Tyr Asn Gly Gly Thr Asp Phe Ser Asn Tyr Glu Asp Glu Ile Tyr Arg
175                 180                 185                 190

Asn Leu Phe Asp Leu Ala Ser Phe Asn His Ile Asn Ser Glu Leu Asn
            195                 200                 205

Asn Tyr Leu Glu Asp Ala Val Lys Lys Trp Leu Asp Leu Gly Ile Asp
            210                 215                 220

Gly Ile Arg Ile Asp Ala Val Ala His Met Pro Pro Gly Trp Lys Lys
225                 230                 235

Ala Tyr Met Asp Thr Ile Tyr Asp His Arg Ala Val Phe Thr Phe Gly
            240                 245                 250

Glu Trp Phe Thr Gly Pro Ser Gly Asn Glu Asp Tyr Thr Lys Phe Ala
255                 260                 265                 270

Asn Asn Ser Gly Met Ser Val Leu Asp Phe Arg Phe Ala Gln Thr Thr
                275                 280                 285

Arg Asn Val Ile Gly Asn Asn Asn Gly Thr Met Tyr Asp Ile Glu Lys
            290                 295                 300
```

```
Met Leu Thr Asp Thr Glu Asn Asp Tyr Asp Arg Pro Gln Asp Gln Val
        305                 310                 315
Thr Phe Leu Asp Asn His Asp Met Ser Arg Phe Thr Asn Gly Gly Glu
        320                 325                 330
Ser Thr Arg Thr Thr Asp Ile Gly Leu Ala Leu Met Leu Thr Ser Arg
335                 340                 345                 350
Gly Val Pro Thr Ile Tyr Tyr Gly Thr Glu Gln Tyr Met Lys Gly Asp
                355                 360                 365
Gly Asp Pro Gly Ser Arg Gly Met Met Ala Ser Phe Asp Glu Asn Thr
                370                 375                 380
Asp Ala Tyr Lys Leu Ile Gln Lys Leu Ala Pro Leu Arg Lys Ser Asn
                385                 390                 395
Pro Ala Tyr Gly Tyr Gly Thr Thr Thr Glu Arg Trp Ile Asn Asp Asp
                400                 405                 410
Val Leu Ile Tyr Glu Arg His Phe Gly Glu Asn Tyr Ala Leu Ile Ala
415                 420                 425                 430
Ile Asn Arg Ser Leu Asn Thr Ser Tyr Asn Ile Gln Gly Leu Gln Thr
                435                 440                 445
Glu Met Pro Ser Asn Ser Tyr Asp Asp Val Leu Asp Gly Leu Leu Asp
                450                 455                 460
Gly Gln Ser Ile Val Val Asp Asn Lys Gly Gly Val Asn Glu Phe Gln
                465                 470                 475
Met Ser Pro Gly Glu Val Ser Val Trp Glu Phe Glu Ala Glu Asn Val
                480                 485                 490
Asp Lys Pro Ser Ile Gly Gln Val Gly Pro Ile Ile Gly Glu Ala Gly
495                 500                 505                 510
Arg Thr Val Thr Ile Ser Gly Glu Gly Phe Gly Ser Ser Gln Gly Thr
                515                 520                 525
Val His Phe Gly Ser Thr Ser Ala Glu Ile Leu Ser Trp Asn Asp Thr
                530                 535                 540
Ile Ile Thr Leu Thr Val Pro Asn Asn Glu Ala Gly Tyr His Asp Ile
                545                 550                 555
Thr Val Val Thr Glu Asp Gln Val Ser Asn Ala Tyr Glu Phe Glu
                560                 565                 570
Val Leu Thr Ala Asp Gln Val Thr Val Arg Phe Ile Ile Asp Asn Ala
575                 580                 585                 590
Glu Thr Lys Leu Gly Glu Asn Val Phe Leu Val Gly Asn Val His Glu
                595                 600                 605
Leu Gly Asn Trp Asp Pro Glu Gln Ser Val Gly Arg Phe Phe Asn Gln
                610                 615                 620
Ile Val Tyr Gln Tyr Pro Thr Trp Tyr Tyr Asp Val Asn Val Pro Ala
                625                 630                 635
Asn Thr Asp Leu Glu Phe Lys Phe Ile Lys Ile Asp Gln Asp Asn Asn
640                 645                 650
Val Ile Trp Gln Ser Gly Ala Asn Gln Thr Tyr Ser Ser Pro Glu Ser
655                 660                 665                 670
Gly Thr Gly Ile Ile Arg Val Asp Trp
                675

<210> SEQ ID NO 3
<211> LENGTH: 42
<212> TYPE: DNA
<213> ORGANISM: Artificial Sequence
<220> FEATURE:
<223> OTHER INFORMATION: Primer #LWN5494
```

```
<220> FEATURE:
<221> NAME/KEY: misc_feature
<223> OTHER INFORMATION: Primer #LWN5494

<400> SEQUENCE: 3
gtcgccgggg cggccgctat caattggtaa ctgtatctca gc                 42

<210> SEQ ID NO 4
<211> LENGTH: 64
<212> TYPE: DNA
<213> ORGANISM: Artificial Sequence
<220> FEATURE:
<223> OTHER INFORMATION: Primer #LWN5495
<220> FEATURE:
<221> NAME/KEY: misc_feature
<223> OTHER INFORMATION: #LWN5495

<400> SEQUENCE: 4
gtcgcccggg agctctgatc aggtaccaag cttgtcgacc tgcagaatga ggcagcaaga    60
agat                                                               64

<210> SEQ ID NO 5
<211> LENGTH: 61
<212> TYPE: DNA
<213> ORGANISM: Artificial Sequence
<220> FEATURE:
<223> OTHER INFORMATION: Primer #LWN5938
<220> FEATURE:
<221> NAME/KEY: misc_feature
<223> OTHER INFORMATION: #LWN5938

<400> SEQUENCE: 5
gtcggcggcc gctgatcacg taccaagctt gtcgacctgc agaatgaggc agcaagaaga    60
t                                                                  61

<210> SEQ ID NO 6
<211> LENGTH: 35
<212> TYPE: DNA
<213> ORGANISM: Artificial Sequence
<220> FEATURE:
<223> OTHER INFORMATION: Primer #LWN5939
<220> FEATURE:
<221> NAME/KEY: misc_feature
<223> OTHER INFORMATION: #LWN5939

<400> SEQUENCE: 6
gtcggagctc tatcaattgg taactgtatc tcagc                         35

<210> SEQ ID NO 7
<211> LENGTH: 35
<212> TYPE: DNA
<213> ORGANISM: Artificial Sequence
<220> FEATURE:
<223> OTHER INFORMATION: Primer #LWN7864
<220> FEATURE:
<221> NAME/KEY: misc_feature
<223> OTHER INFORMATION: #LWN7864

<400> SEQUENCE: 7
aacagctgat cacgactgat cttttagctt ggcac                         35

<210> SEQ ID NO 8
<211> LENGTH: 37
<212> TYPE: DNA
<213> ORGANISM: Artificial Sequence
<220> FEATURE:
<223> OTHER INFORMATION: Primer #LWN7901
```

```
<220> FEATURE:
<221> NAME/KEY: misc_feature
<223> OTHER INFORMATION: #LWN7901

<400> SEQUENCE: 8
aactgcagcc gcggcacatc ataatgggac aaatggg                                    37

<210> SEQ ID NO 9
<211> LENGTH: 83
<212> TYPE: DNA
<213> ORGANISM: Artificial Sequence
<220> FEATURE:
<223> OTHER INFORMATION: Primer 130721
<220> FEATURE:
<221> NAME/KEY: misc_feature
<223> OTHER INFORMATION: Primer 130721

<400> SEQUENCE: 9
cgatcggccg ataaaaaaac cgggcggaaa ccgcccgtca tctggcgcgc ctatataccg           60
cggctgcaga atgaggcagc aag                                                   83

<210> SEQ ID NO 10
<211> LENGTH: 25
<212> TYPE: DNA
<213> ORGANISM: Artificial Sequence
<220> FEATURE:
<223> OTHER INFORMATION: Primer 130722
<220> FEATURE:
<221> NAME/KEY: misc_feature
<223> OTHER INFORMATION: Primer 130722

<400> SEQUENCE: 10
ggcgcattaa cggaataaag ggtgt                                                 25

<210> SEQ ID NO 11
<211> LENGTH: 43
<212> TYPE: DNA
<213> ORGANISM: Artificial Sequence
<220> FEATURE:
<223> OTHER INFORMATION: CGT. Upper. SacII
<220> FEATURE:
<221> NAME/KEY: misc_feature
<223> OTHER INFORMATION: CGT. upper.SacII

<400> SEQUENCE: 11
cattctgcag ccgcggccga agaaaacgca catttaaaaa tcc                             43

<210> SEQ ID NO 12
<211> LENGTH: 45
<212> TYPE: DNA
<213> ORGANISM: Artificial Sequence
<220> FEATURE:
<223> OTHER INFORMATION: CGT. lower.AscI
<220> FEATURE:
<221> NAME/KEY: misc_feature
<223> OTHER INFORMATION: CGT. upper.AscI

<400> SEQUENCE: 12
gctcggcgcg ccttagtata cattcgtttt aagaatttat ttgtc                           45
```

CGTASE AND DNA SEQUENCE ENCODING SAME

CROSS-REFERENCE TO RELATED APPLICATIONS

This application is a 35 U.S.C. 371 national application of PCT/DK01/00494 filed Jul. 13, 2001 (the international application was published under PCT Article 21(2) in English) and claims priority or the benefit under 35 U.S.C. 119 of Danish application nos. 2000 01116 and 2000 01128 filed Jul. 19, 2000 and Jul. 24, 2000, respectively, and U.S. provisional application Nos. 60/221,470 and 60/221,344, both filed on Jul. 26, 2000, the contents of which are fully incorporated herein by reference.

FIELD OF THE INVENTION

The present invention relates to isolated CGTases and isolated nucleic acid sequences encoding the CGTases. The invention also relates to nucleic acid constructs, vectors, and host cells comprising the nucleic acid sequences as well as methods for producing and using the CGTases, in particular to cleaning and detergent composition comprising such CGTases.

BACKGROUND OF THE INVENTION

Cyclomaltodextrin glucanotransferase (E.C. 2.4.1.19), also designated cyclodextrin glucanotransferase or cyclodextrin glycosyltransferase, in the following termed CGTase, catalyses the conversion of starch and similar substrates into cyclomaltodextrins via an intramolecular transglycosylation reaction, thereby forming cyclomaltodextrins, in the following termed cyclodextrins (or CD), of various sizes. Commercially most important are cyclodextrins of 6, 7 and 8 glucose units, which are termed alpha-, beta- and gamma-cyclodextrins, respectively. Commercially less important are cyclodextrins of 9, 10, and 11 glucose units, which are termed delta-, epsilon- and zeta-cyclodextrins, respectively.

Cyclodextrins are thus cyclic glucose oligomers (typically having a from 6 to 11 glucose units) with a hydrophobic internal cavity. They are able to form inclusion complexes with many small hydrophobic molecules in aqueous solutions, resulting in changes in physical properties, e.g. increased solubility and stability and decreased chemical reactivity and volatility. Cyclodextrins find applications particularly in the food, cosmetic, chemical and pharmaceutical industries.

Most CGTases have both starch-degrading activity and transglycosylation activity. Although some CGTases produce mainly alpha-cyclodextrins and some CGTases produce mainly beta-cyclodextrins, CGTases usually form a mixture of alpha-, beta- and gamma-cyclodextrins. Selective precipitation steps with organic solvents may be used for the isolation of separate alpha-, beta- and gamma-cyclodextrins.

Several amino acid sequences encoding peptides showing CGTase activity are known, such as sequences from *Bacillus* spp. (DE4009822) and *Bacillus sterrothermophilius* (EMBL entry no. U83799).

The object of the present invention is to provide novel CGTases, in particular CGTases which are useful in cleaning and detergent composition.

This object is met by the present invention as it has been found that CGTases according to the invention surprisingly exhibit good performance in starch removal when tested under realistic wash conditions.

SUMMARY OF THE INVENTION

Thus, in a first aspect the present invention relates to an isolated cyclomaltodextrin glucanotransferease (CGTase), selected from the group consisting of:
(a) a CGTase having an amino acid sequence which has at least 65% identity with the amino acid sequence shown as amino acids 1 to 679 of SEQ ID NO:2;
(b) a CGTase which is encoded by a nucleic acid sequence which hybridizes under low stringency conditions with
  (i) a complementary strand of the nucleic acid sequence shown as nucleotides 103 to 2139 of SEQ ID NO:1, or
  (ii) a subsequence of (i) of at least 100 nucleotides;
(c) a protein derived from the mature peptide of SEQ ID NO:1 by substitution, deletion or addition of one or several amino acids and having CGTase activity; and
(d) a CGTase which has optimum activity in the pH range of from 8.5 to 9.5.

In a second aspect the present invention relates to an isolated nucleic acid sequence comprising a nucleic acid sequence, which encodes for the CGTase according to the invention.

In a third aspect the present invention relates to an isolated nucleic acid sequence encoding a CGTase, selected from the group consisting of:
(a) a nucleic acid sequence having at least 65% identity with the nucleic acid sequence shown as nucleotides 103 to 2139 of SEQ ID NO:1;
(b) a nucleic acid sequence which hybridizes under low stringency conditions with
  (i) a complementary strand of the nucleic acid sequence shown as nucleotides 103 to 2139 of SEQ ID NO:1, or
  (ii) a subsequence of (i) of at least 100 nucleotides; and
(c) a nucleic acid sequence derived from the mature peptide encoding nucleic acid sequence shown as nucleotides 103 to 2139 of SEQ ID NO:1 by substitution, deletion or addition of one or several amino acids and encoding a protein having CGTase activity.

In a fourth aspect the present invention relates to a nucleic acid construct comprising the nucleic acid sequence according to the invention operably linked to one or more control sequences capable of directing the expression of the CGTase in a suitable expression host.

In a fifth aspect the present invention relates to a recombinant expression vector comprising the nucleic acid construct according to the invention, a promoter, and transcriptional and translational stop signals.

In a sixth aspect the present invention relates to a recombinant host cell comprising the nucleic acid construct according to the invention.

In a seventh aspect the present invention also relates to a cleaning or detergent composition, in particular a laundry or dishwash composition, comprising the CGTase according to the invention.

In an eighth aspect the present invention also relates to a process for preparing a dough or a baked product prepared from the dough which comprises the CGTase according to the invention.

Further aspects of the present invention relates to methods for producing the CGTase as well as to methods for employing and using the CGTase. These as well as other aspects of the present invention will be apparent from the below description and the appended claims.

DETAILED DESCRIPTION OF THE INVENTION

CGTases

Figure 1:
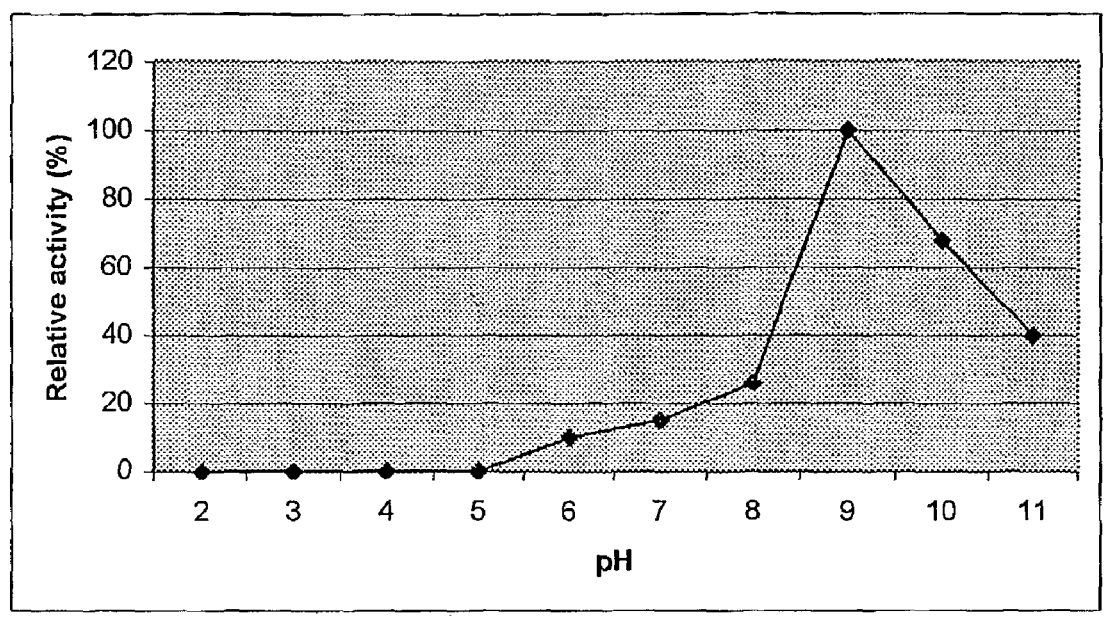
FIG. 1 shows the pH profile of the CGTase of the invention (amino acids 1 to 679 of SEQ ID NO:2).
Figure 2:
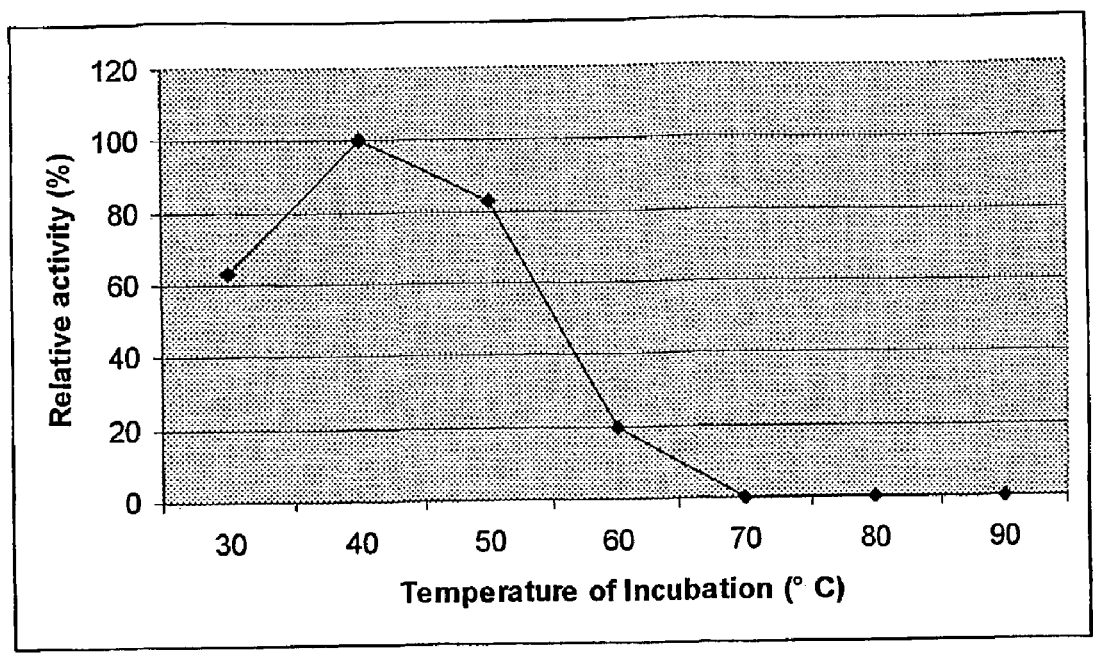
FIG. 2 shows the temperature optimum profile (from 30 to 90° C.) of the CGTase of the invention (amino acids 1 to 679 of SEQ ID NO:2).
Figure 3:
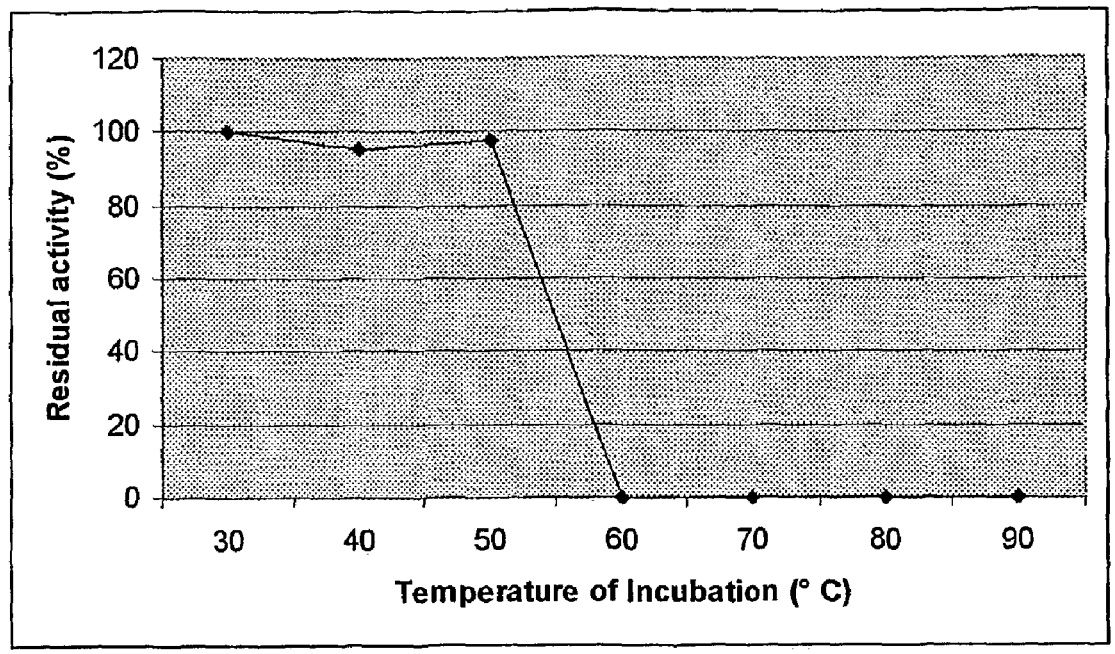
FIG. 3 shows the temperature stability curve (from 30 to 90° C.) of the CGTase of the invention (amino acids 1 to 679 of SEQ ID NO:2).

In a first embodiment of the present invention, the isolated CGTases has an amino acid sequence which has at least 65% identity with the amino acid sequence shown as amino acids 1 to 679 of SEQ ID NO:2 (i.e., the mature CGTase). In an interesting embodiment of the invention the CGTase has at least 70%, at least 75%, at least 80%, at least 85%, at least 90%, at least 95%, at least 96%, at least 97%, at least 98%, or at least 99% identity with the amino acid sequence shown as amino acids 1 to 679 of SEQ ID NO:2 (hereinafter "homologous CGTases").

In a preferred embodiment, the homologous CGTases have an amino acid sequence which differ by no more than ten amino acids, preferably by no more than five amino acids, e.g. by no more than four amino acids, such as by no more than three amino acids, by no more than two amino acids, or by no more than one amino acid from the amino acid sequence shown as amino acids 1 to 679 of SEQ ID NO:2.

The identity between prior art CGTases and the amino acid sequence shown as amino acids 1 to 679 may, for example, be calculated as described in the following: Alignments of sequences and calculation of identity scores can be done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA. While the penalty for additional residues in a gap is −2 for proteins and −4 for DNA. Align is from the fasta package version v20u6 (W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA" Methods in Enzymology 183:63-98).

Preferably, the CGTases of the present invention comprise the amino acid sequence shown as amino acids 1 to 679 of SEQ ID NO:2, or an allelic variant thereof. Obviously, the CGTase of the invention may also consist of the amino acid sequence shown as amino acids 1 to 679 of SEQ ID NO:2.

An allelic variant denotes any of two or more alternative forms of a gene occupying the same chromosomal locus. Allelic variation arises naturally through mutation, and may result in polymorphism within populations. Gene mutations can be silent (no change in the encoded CGTase) or may encode CGTases having altered amino acid sequences. An allelic variant of a CGTase is a CGTase encoded by an allelic variant of a gene.

In a second embodiment of the invention, the isolated CGTase is encoded by a nucleic acid sequence which hybridizes under low stringency conditions, preferably under medium stringency conditions, more preferably under high stringency conditions with (i) a complementary strand of the nucleic acid sequence shown as nucleotides 103 to 2139 of SEQ ID NO:1, or (ii) a subsequence of (i) of at least 100 nucleotides (J. Sambrook, E. F. Fritsch, and T. Maniatus, 1989, *Molecular Cloning, A Laboratory Manual*, $2^{ed}$ edition, Cold Spring Harbor, N.Y.).

The subsequence of the complementary strand of the nucleic acid sequence shown as nucleotides 103 to 2139 of SEQ ID NO:1 may be at least 100 nucleotides or preferably at least 200 nucleotides. Moreover, the subsequence should encode a CGTase fragment. The CGTases may also be allelic variants or fragments of the CGTases.

The nucleic acid sequence of SEQ ID NO:1 or a subsequence thereof, as well as the amino acid sequence of SEQ ID NO:2 or a fragment thereof, may be used to design a nucleic acid probe to identify and clone DNA encoding CGTases from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA, which hybridizes with the probes described above and which encodes a CGTase. Genomic or other DNA from such other organisms may be separated by agarose or polyacrylamide gel electrophoresis, or other separation techniques known by the skilled person. DNA from the libraries or the separated DNA may be transferred to and immobilized on nitrocellulose or other suitable carrier materials. In order to identify a clone or DNA which is homologous with SEQ ID NO:1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO:1, its complementary strand, or a subsequence thereof, under low to high stringency conditions. Molecules to which the nucleic acid probe hybridizes under these conditions are detected using X-ray film.

In a second interesting embodiment, the nucleic acid probe is a nucleic acid sequence which encodes the (mature) CGTase of SEQ ID NO:2, or a subsequence thereof In a third interesting embodiment, the nucleic acid probe is SEQ ID NO:1. In a fourth interesting embodiment, the nucleic acid probe is the mature CGTase coding region of SEQ ID NO:1. For long probes of at least 100 nucleotides in length, low to high stringency conditions are defined as prehybridization and hybridization at 42° C. in 5×SSPE, 0.3% SDS, 200 μg/ml sheared and denatured salmon sperm DNA, and either 25% formamide for low stringency, 35% formamide for medium stringency, or 50% formamide for high stringency, following standard Southern blotting procedures.

For long probes of at least 100 nucleotides in length, the carrier material is finally washed three times each for 15 minutes using 2×SSC, 0.2% SDS preferably at least at 50° C. (low stringency), more preferably at least at 55° C. (medium stringency), even more preferably at least at 65° C. (high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 M ATP, and 0.2 mg of yeast RNA per ml, following standard Southern blotting procedures.

For short probes which are about 15 nucleotides to about 70 nucleotides in length, the carrier material is washed once in 6× SCC plus 0.1% SDS for 15 minutes and twice each for 15 minutes using 6×SSC at 5° C. to 10° C. below the calculated $T_m$.

As indicated above, the CGTase of the invention may be a CGTase having an amino acid sequence of SEQ ID NO:2, wherein one or more amino acid(s) has (have) been substituted by another (other) amino acid(s), wherein one or more amino acid(s) has (have) been deleted, and/or wherein one more amino acid(s) has (have) been inserted.

Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine, methionine and valine), aromatic amino acids (phenylalanine, tryptophan and tyrosine), and small amino acids (glycine, alanine, serine and threonine). Amino acid substitutions that do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

Moreover, CGTases which are also considered as being within the scope of the present invention, are isolated CGTases, preferably in a purified form, having immunochemical identity or partial immunochemical identity to the CGTases having the amino acid sequence of SEQ ID NO:2. The immunochemical properties are determined by immunological cross-reaction identity tests by the well-known Ouchterlony double immunodiffusion procedure. Specifically, an antiserum containing polyclonal antibodies which are immunoreactive or bind to epitopes of the CGTase having the amino acid sequence of SEQ ID NO:2 are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27-31). A CGTase having immunochemical identity is a CGTase which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. A CGTase having partial immunochemical identity is a CGTase which reacts with the antiserum in a partially identical fashion such as partial fusion of precipitates, partially identical precipitate morphology, and/or partially identical electrophoretic mobility using a specific immunochemical technique. A further explanation of partial immuno-chemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual*, Cold Spring Harbor Press, Cold Spring Harbor, N.Y.

A CGTase of the present invention may be obtained from microorganisms of any genus. For purposes of the present invention, the term "obtained from" as used herein in connection with a given source shall mean that the CGTase encoded by the nucleic acid sequence is produced by the source or by a cell in which the nucleic acid sequence from the source has been inserted. In a preferred embodiment, the CGTase is secreted extracellularly.

The CGTase of the present invention may be a bacterial CGTase. For example, the CGTase may be a gram positive bacterial CGTase such as a *Bacillus* CGTase, e.g., a *Bacillus agaradhaeretis, Bacillus alkalophilis, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* CGTase; or a *Streptomyces* CGTase, e.g., a *Streptomyces lividans* or *Streptomyces murinus* CGTase; or a gram negative bacterial CGTase, e.g., an *E. coli* or a *Pseudomonas* sp. CGTase.

In one particular interesting embodiment the CGTase of the invention is derived from *Bacillus agaradhaerens*, preferably the strain of *B. agaradhaerens* previously deposited with and publicly available from the Deutsche Sammlung von Mikroorganismen und Zellkulturen GmbH (DSMZ) under the deposit number DSM 8721. (DSMZ, Mascheroder Weg 1b, D-38124 Braunsweig, Germany).

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such CGTases may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a CGTase has been detected with the probe(s), the sequence may be isolated or cloned by utilizing techniques which are known to those of ordinary skill in the art (see, e.g., Sambrook et al., 1989, supra).

CGTases encoded by nucleic acid sequences of the present invention also include fused polypeptides or cleavable fusion polypeptides in which another polypeptide is fused at the N-terminus or the C-terminus of the CGTases or fragment thereof. A fused polypeptide is produced by fusing a nucleic acid sequence (or a portion thereof) encoding another polypeptide to a nucleic acid sequence (or a portion thereof of the present invention. Techniques for producing fusion polypeptides are known in the art, and include ligating the coding sequences encoding the polypeptides so that they are in frame and that expression of the fused polypeptide is under control of the same promoter(s) and terminator.

The CGTase having the amino acid sequence shown as SEQ ID NO:2, exhibits optimum activity at a pH value about 9. This, in turn, renders this particular CGTase a suitable candidate for being incorporated in detergent compositions, since most wash is carried out under alkaline conditions.

Thus, in another embodiment the CGTase of the present invention has optimum activity in the pH range of from 8.5 to 9.5, preferably in the pH range of from 8.75 to 9.25, e.g. about 9.

Also, the CGTase having the amino acid sequence shown as SEQ ID NO:2, exhibits optimum activity in the temperature range of 30 to 50° C., preferably the temperature range of 35 to 45° C. and more preferably the temperature range of 38 to 42° C., e.g. about 40° C.

Nucleic Acid Sequences

The present invention also relates to isolated nucleic acid sequences, which encode a CGTase of the present invention.

In one interesting embodiment, the nucleic acid sequence has at least 70% identity with the nucleic acid sequence shown as nucleotides 103 to 2139 of SEQ ID NO:1. Preferably, the nucleic acid sequence has at least 75%, at least 80%, at least 85%, at least 90%, at least 95%, at least 96%, at least 97%, at least 98%, or at least 99% identity with the nucleic acid sequence shown as nucleotides 103 to 2139 of SEQ ID NO:1. In another interesting embodiment of the invention the nucleic acid sequence comprises the amino acid sequence shown as nucleotides 103 to 2139 of SEQ ID NO:1, an allelic variant thereof, or a fragment thereof capable of encoding a CGTase according to the invention. Obviously, the nucleic acid sequence may consist of the amino acid sequence shown as nucleotides 103 to 2139 of SEQ ID NO:1.

For purposes of the present invention, the degree of identity between two nucleic acid sequences is determined is described above.

The present invention also encompasses nucleic acid sequences which encode a CGTase having the amino acid sequence of SEQ ID NO:2, which differ from SEQ ID NO:1 by virtue of the degeneracy of the genetic code.

The present invention also relates to isolated nucleic acid sequences encoding a CGTase of the present invention, which hybridize under low stringency conditions, preferably under medium stringency conditions, more preferably under high stringency conditions, with (i) a complementary strand of the nucleic acid sequence shown as nucleotides 103 to 2139 of SEQ ID NO:1, or (ii) a subsequence of (i) of at least 100 nucleotides. The present invention also relates to complementary strands of (i), (ii), and (iii).

The techniques used to isolate or clone a nucleic acid sequence encoding a CGTase are known in the art and include isolation from genomic DNA, preparation from cDNA, or a combination thereof. The cloning of the nucleic acid sequences of the present invention from such genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of *Bacillus agaradhaerens* or another or related organism and may, for example, be an allelic or species variant of the CGTase encoding region of the nucleic acid sequence.

An isolated nucleic acid sequence can, for example, be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the CGTase, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

Modification of a nucleic acid sequence encoding a CGTase of the present invention may be necessary for the synthesis of CGTases substantially similar to the CGTase. The term "substantially similar" to the CGTase refers to non-naturally occurring forms of the CGTase. These polypeptides may differ in some engineered way from the CGTase isolated from its native source, e.g., variants that differ in specific activity, thermostability, pH optimum, or the like. The variant sequence may be constructed on the basis of the nucleic acid sequence presented as the CGTase encoding part of SEQ ID NO:1, e.g., a subsequence thereof, and/or by introduction of nucleotide substitutions which do not give rise to another amino acid sequence of the CGTase encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active CGTase. Amino acid residues essential to the activity of the CGTase encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for CGTase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

Nucleic Acid Constructs

The present invention also relates to nucleic acid constructs comprising a nucleic acid sequence of the present invention operably linked to one or more control sequences capable of directing the expression of the CGTase in a suitable host cell.

An isolated nucleic acid sequence encoding a CGTase of the present invention may be manipulated in a variety of ways to provide for expression of the CGTase. Manipulation of the nucleic acid sequence prior to its insertion into a vector may be desirable or necessary depending on the expression vector. The techniques for modifying nucleic acid sequences utilizing recombinant DNA methods are well known in the art.

The control sequences include all components which are necessary or advantageous for the expression of a CGTase of the present invention. Each control sequence may be native or foreign to the nucleic acid sequence encoding the CGTase. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a CGTase.

The control sequence may be an appropriate promoter sequence, a nucleic acid sequence which is recognized by a host cell for expression of the nucleic acid sequence. The promoter sequence contains transcriptional control sequences which mediate the expression of the CGTase. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyA), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

The control sequence may also be a suitable transcription terminator sequence, a sequence recognized by a host cell to terminate transcription. The terminator sequence is operably linked to the 3' terminus of the nucleic acid sequence encoding the CGTase. Any terminator which is functional in the host cell of choice may be used in the present invention.

The control sequence may also be a suitable leader sequence, a nontranslated region of an mRNA which is important for translation by the host cell. The leader sequence is operably linked to the 5' terminus of the nucleic acid sequence encoding the CGTase. Any leader sequence that is functional in the host cell of choice may be used in the present invention.

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region that codes for an amino acid sequence linked to the amino terminus of a CGTase and directs the encoded CGTase into the cell's secretory pathway. The 5' end of the coding sequence of the nucleic acid sequence may inherently contain a signal peptide coding region naturally linked in translation reading frame with the segment of the coding region which encodes the secreted CGTase. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the CGTase. However, any signal peptide coding region which directs the expressed CGTase into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

The control sequence may also be a propeptide coding region that codes for an amino acid sequence positioned at the amino terminus of a polypeptide. The resultant polypeptide is known as a proenzyme or propolypeptide (or a zymogen in some cases. A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the CGTase relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the CGTase at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol or tetracycline resistance.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the CGTase or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB 10, pE194, pTA1060, and pAMbeta1 permitting replication in *Bacillus*.

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the CGTases.

A vector comprising a nucleic acid sequence of the present invention is introduced into a host cell so that the vector is maintained as a chromosomal integrant or as a self-replicating extra-chromosomal vector as described earlier. The choice of a host cell will to a large extent depend upon the gene encoding the CGTase and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian, insect, plant, or fungal cell. In a preferred embodiment, the host cell is a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a *Candida, Hansenula, Kluyveromyces, Pichia, Saccharomyces, Schizosaccharomyces,* or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbenisis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium,* or *Trichoderma*.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470-1474. Suitable methods for transforming Fusarium species are described by Malardier et al, 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a CGTase of the present invention, the method comprising (a) cultivating a strain from the genus *Bacillus* to produce a supernatant comprising the CGTase; and (b) recovering the CGTase. Preferably, the strain is of the species *Bacillus agaradhaerens*.

The present invention also relates to a method for producing a CGTase of the invention, the method comprising (a) cultivating a recombinant host cell as described above under conditions conducive to the production of the CGTase, and (b) recovering the CGTase from the cells and/or the culture medium.

In the production methods of the present invention, the cells are cultivated in a nutrient medium suitable for production of the CGTase using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the CGTase to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the CGTase is secreted into the nutrient medium, the CGTase can be recovered directly from the medium. If the CGTase is not secreted, it can be recovered from cell lysates.

The CGTases may be detected using methods known in the art that are specific for the CGTases. These detection methods may include use of specific antibodies, formation of an enzyme product, or disappearance of an enzyme substrate. For example, an enzyme assay may be used to determine the activity of the CGTase as described herein.

The resulting CGTase may be recovered by methods known in the art. For example, the CGTase may be recovered from the nutrient medium by conventional procedures including, but not limited to, centrifugation, filtration, extraction, spray-drying, evaporation, or precipitation.

The CGTases of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., *Protein Purification*, J. C. Janson and L. Ryden, Eds, VCH Publishers, New York, 1989).

Industrial Applications

The CGTase of the invention finds application in processes for the manufacture of cyclodextrins for various industrial purposes, particularly in the food, cosmetic, chemical, agrochemical and pharmaceutical industries.

Therefore, in another aspect, the present invention relates to the use of a CGTase according to the invention in a process for the manufacture of cyclodextrins, in particular alpha-, beta-, gamma-, delta-, epsilon- and/or zeta-cyclodextrins (including mixtures thereof). In a more preferred embodiment, the CGTase of the invention is used in a process for the manufacture of alpha-, beta- and gamma-cyclodextrins, or mixtures thereof. In another preferred embodiment, the CGTase of the invention is used in a process for the manufacture of delta-, epsilon- and zeta-cyclodextrins, or mixtures thereof.

The CGTase of the invention may also be used in a process for the manufacture of linear oligosaccharides, in particular linear oligosaccharides of 2 to 12 glucose units, preferably linear oligosaccharides of 2 to 9 glucose units.

In yet another preferred embodiment, the CGTase of the invention may be used for in situ generation of cyclodextrins. The CGTase of the invention may be added to a substrate-containing medium in which the enzyme is capable of forming the desired cyclodextrins. This application is particularly well suited for being implemented in methods of producing baked products, in methods for stabilizing chemical products during their manufacture, and in detergent compositions (see below).

With respect to detergent compositions it is contemplated that the CGTase of the present invention may be useful for removal of retrograded starch from a hard surface or from laundry. As described in J. A. Radley "Starch and its Derivatives", $4^{th}$ Ed. Chapman and Hall Ltd., pp-194-201, retrogradation is a term given to the changes, which occur spontaneously in a starch paste or gel on ageing. It arises from the inherent tendency of starch molecules to bind to one another and which leads to an increase in crystallinity. Solutions of low concentrations become increasingly cloudy due to the progressive association of starch molecules into larger particles. Spontaneous precipitation takes place and the precipitated starch appears to be reverting to its original condition on cold-water insolubility. Pastes of higher concentrations on cooling set to a gel, which on ageing becomes steadily firmer due to the increasing association of starch molecules. This arises because of the strong tendency for hydrogen bond formation between hydroxy groups on adjacent starch molecules.

The changes taking place during retrogradation are of considerable importance in the industrial uses of starch. It is believed to be an important factor in the staling of bread and in the textural changes of other starch-containing foods, e.g. canned soups, peas, meat preparations, etc. Starch and retrograded starch are also found in the textile, paper and adhesives industries. Indeed, fabrics are sized with starch in the textile process. Depending on the sizing process, retrograded starch can be formed on the fabrics and might not be removed in the ulterior desizing process. Moreover, the majority of the stains/soils found on fabrics contain starch which upon ageing (in, for example the laundry basket) will retrograde to such associated starchy network. Hence, such retrograded starch-containing materials are found later on the fabric to be cleaned. Furthermore, it has observed tat such retrograded starch entraps further dirt and, hen found on a fabric surface, leads to dingy appearance of the surface to be cleaned.

The CGTase of the invention may also be used for implementation into bread-improving additives, e.g. dough compositions, dough additives, dough conditioners, pre-mixes, and similar preparations conventionally used for adding to the flour and/or the dough during processes for making bread or other baked products. GCTase finds potential application for retarding or preventing retrogradation, and thus the staling, of starch based food common in the baking industry. Also, the use of CGTase may results in an increased volume and an improved crumb structure and softness of the baked product, as well as an increased strength, stability and reduced stickiness and thereby improved machinability of the dough. The effect on the dough can be found to be particularly good when a poor quality flour is used.

Cyclodextrins have an inclusion ability useful for stabilization, solubilization, etc. Thus cyclodextrins can make oxidizing and photolytic substances stable, volatile substances non-volatile, poorly soluble substances soluble, and odoriferous substances odorless, etc. and thus are useful to encapsulate perfumes, vitamins, dyes, pharmaceuticals, pesticides and fungicides. Cyclodextrins are also capable of binding lipophilic substances such as cholesterol, to remove them from egg yolk butter, etc.

Cyclodextrins also find utilization in products and processes relating to plastics and rubber, where they have been used for different purposes in plastic laminates, films, membranes, etc. Also cyclodextrins have been used for the manufacture of biodegradable plastics.

Cleaning and Detergent Compositions

In general, cleaning and detergent compositions are well described in the art and reference is made to WO 96/34946; WO 97/07202; and WO 95/30011 for further description of suitable cleaning and detergent compositions.

The CGTase of the invention may be added to, and thus become a component of, a detergent composition.

The composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising a CGTase enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, a peroxidase, and/or another CGTase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Preferred commercially available protease enzymes include Alcalase™, Savinase™, Primase™, Duralase™, Esperase™, and Kannase™ (Novozymes A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis*

(WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Preferred commercially available lipase enzymes include Lipolase™ and Lipolase Ultra™ (Novozymes A/S).

Amylases: Suitable amylases (alpha and/or beta) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839.

Commercially available amylases are Duramyl™, Termamyl™, Fungamyl™ and BAN™ (Novozymes A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940.

Commercially available cellulases include Celluzyme™, and Carezyme™ (Novozymes A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol or a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition typically comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202, which is hereby incorporated as reference.

The invention is described in further detail in the following examples, which are not in any way intended to limit the scope of the invention as claimed.

In the detergent compositions, the abbreviated component identifications have the following meanings:

| | |
|---|---|
| LAS: | Sodium linear $C_{12}$ alkyl benzene sulphonate |
| TAS: | Sodium tallow alkyl sulphate |
| XYAS: | Sodium $C_{1X}$-$C_{1Y}$ alkyl sulfate |
| SS: | Secondary soap surfactant of formula 2-butyl octanoic acid |
| 25EY: | A $C_{12}$-$C_{15}$ predominantly linear primary alcohol condensed with an average of Y moles of ethylene oxide |
| 45EY: | A $C_{14}$-$C_{15}$ predominantly linear primary alcohol condensed with an average of Y moles of ethylene oxide |
| XYEZS: | $C_{1X}$-$C_{1Y}$ sodium alkyl sulfate condensed with an average of Z moles of ethylene oxide per mole |
| Nonionic: | $C_{13}$-$C_{15}$ mixed ethoxylated/propoxylated fatty alcohol with an average degree of ethoxylation of 3.8 and an average degree of propoxylation of 4.5 sold under the tradename Plurafax LF404 by BASF GmbH |
| CFAA: | $C_{12}$-$C_{14}$ alkyl N-methyl glucamide |
| TFAA: | $C_{16}$-$C_{18}$ alkyl N-methyl glucamide |
| Silicate: | Amorphous Sodium Silicate ($SiO_2$:$Na_2O$ ratio = 2.0) |
| NaSKS-6: | Crystalline layered silicate of formula $\delta$-$Na_2Si_2O_5$ |
| Carbonate: | Anhydrous sodium carbonate |
| Phosphate: | Sodium tripolyphosphate |
| MA/AA: | Copolymer of 1:4 maleic/acrylic acid, average molecular weight about 80,000 |
| Polyacrylate: | Polyacrylate homopolymer with an average molecular weight of 8,000 sold under the tradename PA30 by BASF Gmbh |
| Zeolite A: | Hydrated Sodium Aluminosilicate of formula $Na_{12}(AlO_2SiO_2)_{12} \cdot 27H_2O$ having a primary particle size in the range from 1 to 10 micrometers |
| Citrate: | Tri-sodium citrate dihydrate |
| Citric: | Citric Acid |
| Perborate: | Anhydrous sodium perborate monohydrate bleach, empirical formula $NaBO_2 \cdot H_2O_2$ |
| PB4: | Anhydrous sodium perborate tetrahydrate |
| Percarbonate: | Anhydrous sodium percarbonate bleach of empirical formula $2Na_2CO_3 \cdot 3H_2O_2$ |
| TAED: | Tetraacetyl ethylene diamine |
| CMC: | Sodium carboxymethyl cellulose |
| DETPMP: | Diethylene triamine penta (methylene phosphonic acid), marketed by Monsanto under the Tradename Dequest 2060 |
| PVP: | Polyvinylpyrrolidone polymer |
| EDDS: | Ethylenediamine-N, N'-disuccinic acid, [S,S] isomer in the form of the sodium salt |
| Suds Suppressor: | 25% paraffin wax Mpt 50° C., 17% hydrophobic silica, 58% parafin oil |
| Granular Suds Suppressor: | 12% Silicone/silica, 18% stearyl alcohol, 70% starch in granular form |
| Sulphate: | Anhydrous sodium sulphate |
| HMWPEO: | High molecular weight polyethylene oxide |
| TAE 25: | Tallow alcohol ethoxylate (25) |

Detergent Example I

A granular fabric cleaning composition in accordance with the invention may be prepared as follows:

| | |
|---|---|
| Sodium linear $C_{12}$ alkyl benzene sulfonate | 6.5 |
| Sodium sulfate | 15.0 |
| Zeolite A | 26.0 |
| | 28 |
| Sodium nitrilotriacetate | 5.0 |
| Enzyme | 0.1 |
| PVP | 0.5 |
| TAED | 3.0 |
| Boric acid | 4.0 |
| Perborate | 18.0 |
| Phenol suiphonate | 0.1 |
| Minors | up to 100% |

Detergent Example II

A compact granular fabric cleaning composition (density 800 g/l) in accordance with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme | 0.1 |
| TAED | 6.0 |
| Percarbonate | 22.0 |
| EDDS | 0.3 |
| Granular suds suppressor | 3.5 |
| water/minors | up to 100% |

Detergent Example III

Granular fabric cleaning compositions in accordance with the invention, which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10.0 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme | 0.1 | 0.05 |
| Silicate | 2.5 | — |
| Sulphate | 5.2 | 3.0 |
| PVP | 0.5 | — |
| Poly(4-vinylpyridine)-N-Oxide/copolymer of vinyl-imidazole and vinyl-pyrrolidone | — | 0.2 |
| Perborate | 1.0 | — |
| Phenol sulfonate | 0.2 | — |
| Water/Minors | up to 100% | |

Detergent Example IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 4.0 | 4.0 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme | 0.1 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | up to 100% | |

Detergent Example V

Heavy duty liquid fabric cleaning compositions in accordance with the invention may be prepared as follows:

| | | |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme | 0.10 | 0.05 |
| Coco-alkyl dimethyl hydroxy ethyl ammonium chloride | — | 3.0 |
| Smectite clay | — | 5.0 |
| PVP | 2.0 | — |
| Water/Minors | up to 100% | |

Materials and Methods

Molecular cloning techniques are described in J. Sambrook, E. F. Fritsch, and T. Maniatis, 1989, *Molecular Cloning, A Laboratory Manual,* 2nd Edition, Cold Spring Harbor, N.Y.

Chemicals used as buffers and substrates were commercial products of at least reagent grade.

The composition of TY Medium is described in F. M. Ausubel et al. (Ed.), 1995, *Current Protocols in Molecular Biology*, John Wiley and Sons.

The composition of LB Agar is described in F. M. Ausubel et al. (Ed.), 1995, *Current Protocols in Molecular Biology*, John Wiley and Sons.

LBPG is LB agar supplemented with 0.5% glucose and 0.05M potassium phosphate, pH 7.0.

BPX Media is described in EP 0 506 780.

Activity Determination

Assays traditionally developed and used for determining α-amylase activity may also be applied for determination of CGTase activity.

Thus, in the present context one Kilo alpha-amylase Unit (1 KNU) is the amount of CGTase which breaks down 5.26 g starch based upon the following condition:

| | |
|---|---|
| Substrate | soluble starch |
| Calcium content in solvent | 0.0043M |
| Reaction time | 7-20 minutes |
| Temperature | 37° C. |
| pH | 5.6 |

Assay for CGTase (α-Amylase) Activity

CGTase activity is determined by a method employing Phadebas® tablets as substrate. Phadebas tablets (Phadebas® Amylase Test, supplied by Pharmacia Diagnostic) contain a cross-linked insoluble blue-coloured starch polymer, which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The CGTase to be tested is diluted appropriately in 50 mM Britton-Robinson buffer. 1 ml of this CGTase solution is added to the 5 ml 50 mM Britton-Robinson buffer. The starch is hydrolysed by the CGTase, giving soluble blue fragments. The absorbance of the resulting blue solution, measured spectrophotometrically at 620 nm, is directly proportional to the CGTase activity.

Strains

*Bacillus agaradhaerens* (DSM 8721) comprises the CGTase encoding DNA sequence of the invention.

*B. subtilis* PL1801. This strain is the *B. subtilis* DN1885 with disrupted apr and npr genes (B. Diderichsen, U. Wedsted, L. Hedegaard, B. R. Jensen, C. Sjøholm (1990) *Cloning of aldB, which encodes alpha-acetolactate decarboxylase, an exoenzyme from Bacillus brevis.* J. Bacteriol., 172, 4315-4321).

Competent cells were prepared and transformed as described by R. E. Yasbin, G. A., Wilson, and F. E. Young (1975) *Transformation and transfection in lysogenic strains of Bacillus subtilis: evidence for selective induction of prophage in competent cells.* J. Bacteriol, 121:296-304.

Plasmids pMOL944: This plasmid is a pUB110 derivative essentially containing elements making the plasmid propagatable in *Bacillus subtilis*, kanamycin resistance gene and having a strong promoter and signal peptide cloned from the amyL gene of *B. licheniformis* ATCC14580. The signal peptide contains a SacII site making it convenient to clone the DNA encoding the mature part of a protein in-fusion with the signal peptide. This results in the expression of a Pre-protein which is directed towards the exterior of the cell.

The plasmid was constructed by means of ordinary genetic engineering and is briefly described in the following.

Construction of pMOL944: The pUB110 plasmid (T. McKenzie, et al., 1986, Plasmid 15:93-103) was digested with the unique restriction enzyme NciI. A PCR fragment amplified from the amyL promoter encoded on the plasmid pDN1981 (P. L. Jørgensen et al., 1990, Gene, 96, pp. 37-41) was digested with NciI and inserted in the NciI digested pUB110 to give the plasmid pSJ2624.

The two PCR primers used were # LWN5494 (SEQ ID NO:3) and # LWN5495 (SEQ ID NO:4). The primer #LWN5494 inserts a NotI site in the plasmid.

The plasmid pSJ2624 was then digested with SacI and NotI and a new PCR fragment amplified on amyL promoter encoded on the pDN1981 was digested with SacI and NotI and this DNA fragment was inserted in the SacI-NotI digested pSJ2624 to give the plasmid pSJ2670.

This cloning replaces the first amyL promoter cloning with the same promoter but in the opposite direction. The two primers used for PCR amplification were #LWN5938 (SEQ ID NO:5) and #LWN5939 (SEQ ID NO:6).

The plasmid pSJ2670 was digested with the restriction enzymes PstI and BclI and a PCR fragment amplified from a cloned DNA sequence encoding the alkaline amylase described in WO 95/26397 was digested with PstI and BclI and inserted to give the plasmid pMOL944. The two primers used for PCR were #LWN7864 (SEQ ID NO:7) and #LWN7901 (SEQ ID NO:8). The primer #LWN7901 inserts a SacII site in the plasmid.

pPL3143: This plasmid is a pMOL944 derivative in which a terminator has been inserted between the SacII and the NotI site in pMOL944. At the same time a new restriction site for cloning AscI has been inserted.

The plasmid was constructed by means of ordinary genetic engineering and is briefly described in the following.

Construction of pPL3143: The plasmid pMOL944 was digested with SacII and NotI. A PCR fragment generating a terminator was made using the two primers Primer 130721 (SEQ ID NO:9) and Primer 130722 (SEQ ID NO:10) and plasmid pMOL944 as template. This fragment was digested with EagI and SacII and inserted between the SacII and the NotI site in PMOL944 to create the plasmid pPL3143.

Cloning of the Bacillus agaradhaerens CGTase Gene

Genomic DNA preparation: Strain Bacillus agaradhaerens DSM 8721 was propagated in liquid TY medium (pH adjusted to 9 by addition of sodium hydrogen carbonate (NaHCO$_3$)). After 16 hours incubation at 30° C. and 300 rpm, the cells were harvested, and genomic DNA isolated by the method described by Pitcher et al. (D. G Pitcher, N. A. Saunders, R. J. Owen (1989) *Rapid extraction of bacterial genomic DNA with guanidium thiocyanate.* Lett. Appl. Microbiol., 8, 151-156).

Subcloning and expression of the CGTase gene from *B. agaradhaerens* in *B. subtilis*: The CGTase encoding DNA sequence of the invention was PCR amplified using the PCR primer set consisting of the two oligo nucleotides CGT. upper. SacII (SEQ ID NO:11) and CGT. lower. AscI (SEQ ID NO:12). The two oligo nucleotides contain the restriction site SacII and AscI respectively.

Chromosomal DNA isolated from *B. agaradhaerens* as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM MgCl$_2$, 0.01% (w/v) gelatin) containing 200 µM of each dNTP, 2.5 units of AmpliTaq polymerase (Perkin-Elmer, Cetus, USA) and 100 pmol of each primer The PCR reactions was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. 5 µl aliquots of the amplification product were analysed by electrophoresis in 0.7% agarose gels (NuSieve, FMC). The appearance of a DNA fragment size approx. 2.1 kb indicated proper amplification of the gene segment.

45 µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5.

5 µg of pMOL944 and 25 µl of the purified PCR fragment was digested with SacII and AscI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the SacII-AscI digested and purified pMOL944. The ligation was performed overnight at 16° C. using 0.5 µg of each DNA fragment, 1 U of T4 DNA ligase and T4 ligase buffer (Boehringer Mannheim, Germany).

The ligation mixture was used to transform competent *B. subtilis* PL1801. The transformed cells were plated onto LBPG-agar plates containing 10 µg/ml of Kanamycin and 0.5% soluble starch. After 18 hours incubation at 37° C. colonies were seen on plates. Clear halos on a blue background were seen around positive colonies expressing the CGTase gene when adding iodine vapour to the plates. Plasmid DNA from overnight broth cultures was isolated from several positive clones and the plasmid composition analysed by restriction analysis.

One clone having the expected composition was restreaked several times on agar plates as used above. This clone was called PL3468. The clone PL3468 was grown overnight in TY-10 µg/ml Kanamycin at 37° C., and next day 1 ml of cells were used to isolate plasmid from the cells using the Qiaprep Spin Plasmid Miniprep Kit #27106 according to the manufacturers recommendations for *B. subtilis* plasmid preparations. This DNA was DNA sequenced and revealed that the plasmid named pPL3468 contained the DNA sequence corresponding to the CGTase gene shown in SEQ ID NO:1.

Expression and Purification of CGTase

PL3468 was grown in 25×200 ml BPX media with 10 µg/ml of Kanamycin in 500 ml two baffled shakeflasks for 5 days at 37° C. at 300 rpm. The culture supernatant was centrifuged on a Sorvall RC-3B centrifuge, equipped with a GSA rotor head (4500 rpm for 35 min at 4° C.). The CGTase was purified on alpha-cyclodextrin coupled to activated agarose. The centrifuged culture supernatant was applied to an alpha-cyclodextrin-agarose column (1.6×10 cm) in 50 mM sodium acetate, 1 mM CaCl$_2$, 0.5 M NaCl, pH 6.0 at a flow rate of 300 ml h$^{-1}$. The column was washed using 50 mM sodium acetate, 1 mM CaCl$_2$, 0.5 M NaCl, pH 6.0 (approx. 10 column volumes) and the CGTase was subsequently eluted in the same buffer containing 1% (w/v) alpha-cyclodextrin. The CGTase was homogenous as estimated using SDS-PAGE. Protein concentrations were determined spectrophotometrically at 280 nm using a molecular extinction coefficient of Epsilon=124130 M$^{-1}$cm$^{-1}$, and a molecular weight of 80 kDa.

Enzyme Activity Measurements (Phadebas® Blue Starch)

1000 µl buffer containing insoluble blue starch (11 mg/ml) is pre-incubated at 60° C. The enzymatic reaction is initiated by addition of 25 µl enzyme solution. The activity is quenched after 15 min incubation at 60° C. by addition of 250 µl 1 M NaOH. After centrifugation or filtration, the absorbance is measured at 650 nm. NU is defined as DeltaA$_{650}$×min$^{-1}$ at 60° C. and a given pH-value.

Temperature Optimum

The temperature optimum was determined by measuring the enzymatic activity at 30, 40, 50, 60, 70, 80, and 90° C. using Phadebas blue starch at pH 9.0.

Thermostability

Thermostability was determined by incubating the enzymes at varying temperatures (30° C.-90° C.) in 50 mM Hepes, 1 mM CaCl$_2$, pH 9.0 for 5 min. The residual activity was determined as described above. $T_m$ is defined as the temperature where 50% of the starting activity is retained.

pH Activity Dependence

The pH activity dependence was determined using Phadebas blue starch at 10 different pH values ranging from pH 2.0 to 11.0 using the following buffers: 50 mM glycine, 1 mM CaCl$_2$, pH 2.0; 50 mM sodium acetate, 1 mM CaCl$_2$, pH 3.0; 50 mM sodium acetate, 1 mM CaCl$_2$, pH 4.0; 50 mM sodium acetate, 1 mM CaCl$_2$, pH 5.0; 50 mM sodium acetate, 1 mM CaCl$_2$, pH 6.0; 50 mM Hepes, 1 mM CaCl$_2$, pH 7.0; 50 mM Hepes, 1 mM CaCl$_2$, pH 8.0; 50 mM Hepes, 1 mM CaCl$_2$, pH 9.0; 50 mM Caps, 1 mM CaCl$_2$, pH 10.0; 50 mM Caps, 1 mM CaCl$_2$, pH 11.0

Enzyme Digests

Degradation of 0.5% (w/v) amylopectin (Waxy maize) was performed in 5 mM Hepes, 1 mM CaCl$_2$, pH 9.0 at 40° C. The enzymatic reaction was initiated by addition of a 400 μl enzyme solution (dosed based on activity and containing typically around 20 NU/ml; approx. 150 NU/g DS) into a total reaction volume of 10.000 μl. At suitable time intervals (i.e. 1, 2, and 24 hours) the content of cyclodextrins and linear maltooligosaccharide were determined by HPLC.

HPLC Analysis of Starch Hydrolysates

Cyclodextrins and linear maltooligosaccharides were identified and quantified by HPLC (Waters, Milford, USA) using two BioRad Hercules, USA) Aminex HPX-42A (7.8× 300 mm) columns connected in series and operated at 85° C. in water. Sample aliquots of 10 μl were applied to the column using a Waters 717 plus autosampler, the oligosaccharides were eluted isocratically at 0.6 ml/min (Waters 515 HPLC pump) and quantitated using a Waters 410 differential refractometer. The following compounds were formed:

| | |
|---|---|
| Alpha-cyclodextrin: | — |
| Beta-cyclodextrin: | 79% |
| Gamma-cyclodextrin: | 21% |

The invention claimed is:

1. An isolated cyclomaltodextrin glucanotransferase (CGTase), comprising:

(a) a CGTase having an amino acid sequence which has at least 95% identity with the amino acid sequence shown as amino acids 1 to 679 of SEQ ID NO:2; or (b) a CGTase which is encoded by a nucleic acid sequence which hybridizes under high stringency conditions with a complementary strand of the nucleic acid sequence shown as nucleotides 103 to 2139 of SEQ ID NO:1 under hybridization conditions comprising hybridizing in a solution of 5×SSPE, 0.3% SDS, 200 μg/ml of sheared and denatured salmon sperm DNA, and 50% formamide, followed by washing in 2×SSC, 0.2% SDS for 15 minutes at a temperature of 65° C.

2. The CGTase of claim 1, having an amino acid sequence which has at least 95% identity with the amino acid sequence shown as amino acids 1 to 679 of SEQ ID NO:2.

3. The CGTase of claim 1, having an amino acid sequence which has at least 97% identity with the amino acid sequence shown as amino acids 1 to 679 of SEQ ID NO:2.

4. The CGTase of claim 1, having an amino acid sequence which has at least 98% identity with the amino acid sequence shown as amino acids 1 to 679 of SEQ ID NO:2.

5. The CGTase of claim 1, having an amino acid sequence which has at least 99% identity with the amino acid sequence shown as amino acids 1 to 679 of SEQ ID NO:2.

6. The CGTase of claim 1, comprising the amino acid sequence shown as amino acids 1 to 679 of SEQ ID NO:2.

7. The CGTase of claim 1, consisting of the amino acid sequence shown as amino acids 1 to 679 of SEQ ID NO:2.

8. The CGTase of claim 1, comprising an amino acid sequence which is encoded by a nucleic acid sequence which hybridizes under high stringency conditions with a complementary strand of the nucleic acid sequence shown as nucleotides 103 to 2139 or SEQ ID NO:1 under hybridization conditions comprising hybridizing in a solution of 5×SSPE, 0.3% SDS, 200 µg/ml of sheared and denatured salmon sperm DNA, and 50% formamide, followed by washing in 2×SSC, 0.2% SDS for 15 minutes at a temperature of 65° C.

9. The CGTase of claim 1, which is obtained from the genus *Bacillus*.

* * * * *